(12) United States Patent
Schieker et al.

(10) Patent No.: US 10,406,231 B2
(45) Date of Patent: Sep. 10, 2019

(54) CHAIN-EXTENDING POLOXAMERS, THERMOREVERSIBLE HYDROGELS FORMED BY THEM WHICH INCLUDE BIOLOGICAL MATERIALS, AND MEDICINAL APPLICATIONS OF SAME

(71) Applicant: Matthias Schieker, Munich (DE)

(72) Inventors: Matthias Schieker, Munich (DE); Hinrich Wiese, Unna (DE); Uta Moll, Feldkirchen (DE)

(*) Notice: Subject to any disclaimer, the term of this patent is extended or adjusted under 35 U.S.C. 154(b) by 0 days.

(21) Appl. No.: 14/653,194

(22) PCT Filed: Dec. 17, 2013

(86) PCT No.: PCT/EP2013/076966
§ 371 (c)(1),
(2) Date: Jun. 17, 2015

(87) PCT Pub. No.: WO2014/095915
PCT Pub. Date: Jun. 26, 2014

(65) Prior Publication Data
US 2015/0335749 A1   Nov. 26, 2015

(30) Foreign Application Priority Data
Dec. 17, 2012  (DE) .................. 10 2012 223 416

(51) Int. Cl.
| | | |
|---|---|---|
| *A61K 47/10* | (2017.01) | |
| *C08G 18/48* | (2006.01) | |
| *A61K 35/28* | (2015.01) | |
| *A61K 51/06* | (2006.01) | |
| *C12N 5/0775* | (2010.01) | |
| *A61K 51/12* | (2006.01) | |
| *A61K 47/34* | (2017.01) | |
| *C08J 3/075* | (2006.01) | |
| *C08G 18/73* | (2006.01) | |
| *C08G 18/76* | (2006.01) | |
| *C08L 75/08* | (2006.01) | |
| *C08L 89/06* | (2006.01) | |
| *A61K 9/06* | (2006.01) | |
| *A61K 38/18* | (2006.01) | |
| *A61K 38/39* | (2006.01) | |
| *A61K 35/14* | (2015.01) | |
| *C08L 5/00* | (2006.01) | |
| *C08L 5/08* | (2006.01) | |
| *C08L 89/00* | (2006.01) | |
| *C08G 65/333* | (2006.01) | |

(52) U.S. Cl.
CPC ............... *A61K 47/10* (2013.01); *A61K 9/06* (2013.01); *A61K 35/14* (2013.01); *A61K 35/28* (2013.01); *A61K 38/18* (2013.01); *A61K 38/1808* (2013.01); *A61K 38/1841* (2013.01); *A61K 38/1875* (2013.01); *A61K 38/39* (2013.01); *A61K 47/34* (2013.01); *A61K 51/06* (2013.01); *A61K 51/1213* (2013.01); *C08G 18/4804* (2013.01); *C08G 18/4808* (2013.01); *C08G 18/4841* (2013.01); *C08G 18/73* (2013.01); *C08G 18/7671* (2013.01); *C08G 65/33348* (2013.01); *C08J 3/075* (2013.01); *C08L 5/00* (2013.01); *C08L 5/08* (2013.01); *C08L 75/08* (2013.01); *C08L 89/00* (2013.01); *C08L 89/06* (2013.01); *C12N 5/0662* (2013.01); *C08G 2210/00* (2013.01); *C08G 2650/58* (2013.01); *C08J 2389/06* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 3,767,040 A | 10/1973 | Tushaus | |
| 4,039,724 A | 8/1977 | Gobran | |
| 4,423,201 A | 12/1983 | Hicks | |
| 4,608,201 A | 8/1986 | McCollum | |
| 6,629,947 B1* | 10/2003 | Sahatjian | A61B 17/12022 604/11 |
| 2005/0123520 A1* | 6/2005 | Eavey | A61L 27/20 424/93.7 |
| 2005/0175573 A1 | 8/2005 | Pagnoux | |
| 2006/0051384 A1* | 3/2006 | Scholz | A01N 37/02 424/405 |

FOREIGN PATENT DOCUMENTS

| | | |
|---|---|---|
| WO | 1997005185 | 2/1997 |
| WO | 2005051428 | 6/2005 |

OTHER PUBLICATIONS

Chaibundit et al. "Effect of Ethanol on the Micellization and Gelation of Pluronic P123", 2008, Langmuir, 24, pp. 12260-12266.*
http://www.merriamwebster.com /dictionary/derivative retrieved on Dec. 9, 2015.*
https://en.wikipedia.org/ wiki/Poloxamer_407printed online May 8, 2017.*
Elias Volkmer et al: "Poloxamer-based hydrogels hardening at body core temperature as carriers for cell based therapies: in vitro and in vivo analysis", Journal of Materials Science: Materials in Medicine, Bd. 24, Nr. 9, May 28, 2013 (May 28, 2013), Seiten 2223-2234, XP055098779, ISSN: 0957-4530, DOI: 10.1007/s10856-013-4966-6.

(Continued)

*Primary Examiner* — James W Rogers
(74) *Attorney, Agent, or Firm* — Shane Cortesi

(57) ABSTRACT

According to the invention, thermoreversible hydrogels are provided, which are prepared from chain-extended poloxamers, having advantageous properties. In addition, the invention provides thermoreversible hydrogels, including biological materials, and a process for the preparation thereof, thermoreversible hydrogels including living cells, application systems for pharmaceutical applications, and an in-vitro-method for forming a composition on a surface.

2 Claims, 13 Drawing Sheets

(56) References Cited

OTHER PUBLICATIONS

Jun Jiang et al: "Rheology of Thermoreversible Hydrogels from Multiblock Associating Copolymers", Macromolecules, Bd. 41, Nr. 10, May 2008 (May 2008), Seiten 3646-3652, XP055098469, ISSN: 0024-9297, DOI: 10.1021/ma800192m in der Anmeldung erwähnt.
Lan P N et al: "Synthesis and characterization of segmented polyurethanes based on amphiphilic polyether diols", Biomaterials, Elsevier Science Publishers BV., Barking, GB, Bd. 17, Nr. 23, 1996, Seiten 2273-2280, XP004069063, ISSN: 0142-9612, DOI: 10.1016/0142-9612(96)00056-7.
Van Bos M et al: "Hydrophilic polyurethanes for the preparation of drug delivery systems", Acta Pharmaceutica Technologica, Stuttgart, DE, Bd. 33, Nr. 3, 1987, Seiten 120-125, XP002970383, ISSN: 0340-3157.

\* cited by examiner

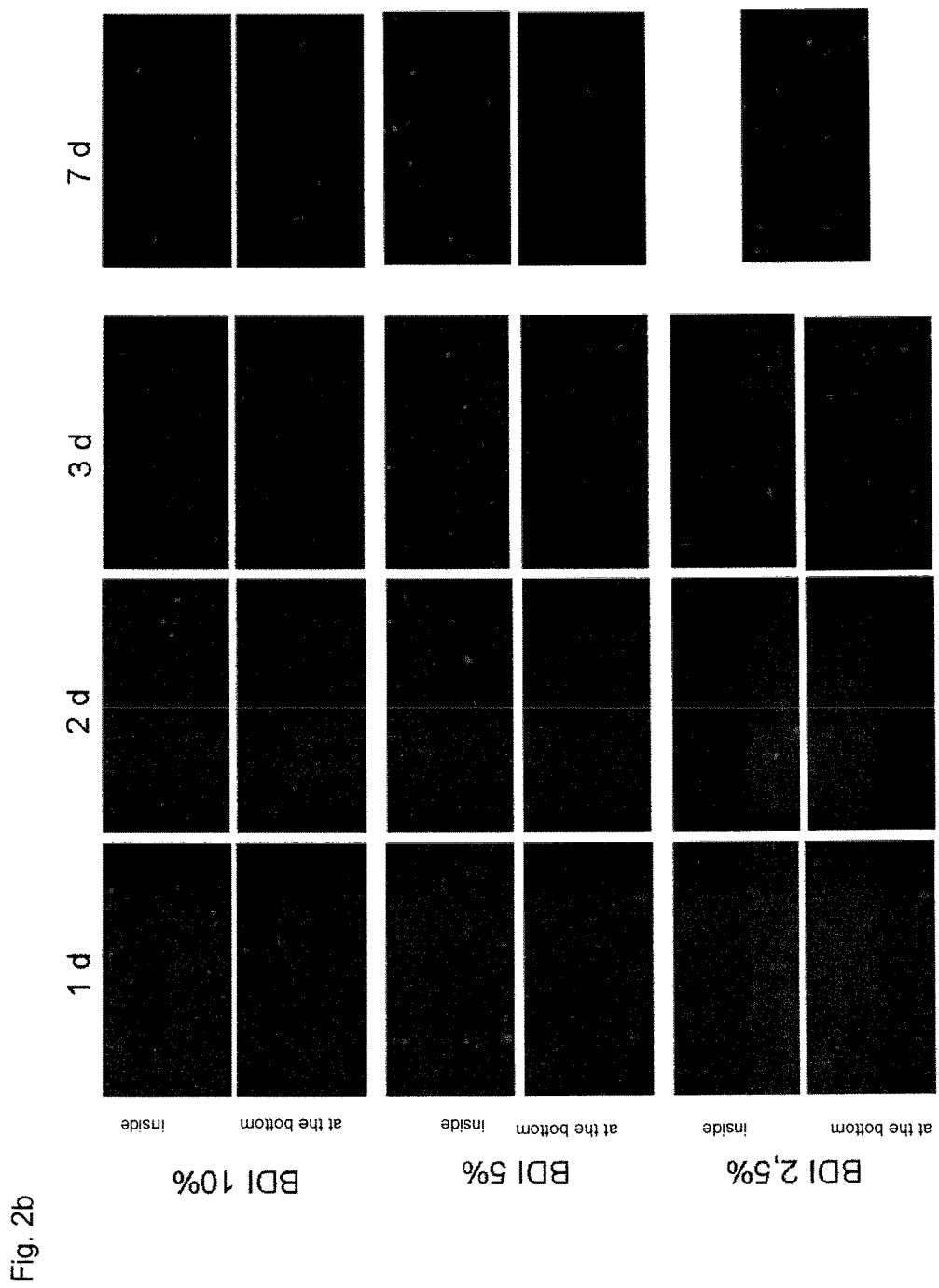

CHAIN-EXTENDING POLOXAMERS, THERMOREVERSIBLE HYDROGELS FORMED BY THEM WHICH INCLUDE BIOLOGICAL MATERIALS, AND MEDICINAL APPLICATIONS OF SAME

FIELD OF THE INVENTION

The invention relates to chain-extended poloxamers. In particular, the invention relates to thermoreversible hydrogels prepared from such chain-extended poloxamers. Moreover, the invention relates to thermoreversible hydrogels which include biological materials and a method for the preparation thereof, application systems for pharmaceutical applications, and an in-vitro method for forming a composition on a surface.

BACKGROUND OF THE INVENTION

The term "poloxamer" refers to a class of polyoxyethylene-polyoxypropylene-block copolymers (first mentioned in U.S. Pat. No. 3,740,421), which are also known under the trade name "Pluronic®" or "Lutrol®" (trademark of BASF SE). These are block copolymers consisting of hydrophilic polyethylene glycol outer blocks and hydrophobic polypropylene glycol inner blocks, i.e. (poly(ethylene oxide)-poly(propylene oxide)-poly(ethylene oxide)-tri-block copolymers, which can be broadly summarised by the following structure:

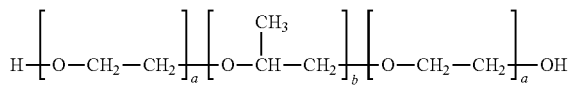

These block copolymers form sols or gels in water by phase separation: The polyethylene glycol blocks dissolve in water, while the polypropylene glycol blocks become associated with one another. This process is called micelle formation. While the micelles are present in a relatively disordered state at a lower temperature (sol state), an ordered formation of these micelles is brought about when the temperature increases, which results in the solidification of the liquid (gel state) (see Alexandridis P., Holzwarth J. F., Hatton T. A. Micellization of Poly(ethylene oxide)-Poly(propylene oxide)-Poly(ethylene oxide) Triblock Copolymers in Aqueous Solutions: Thermodynamics of Copolymer Association. Macromolecules. 1994; 27(9):2414-25). Such gels are therefore also referred to as thermoreversible hydrogels.

Hydrogels based on poloxamers have been known for quite some time (cf. J., Swafford W. B.: Pluronics as a suppository base. Am. J. Pharm. Sci. Support. Public Health. 1960; 132:301-303). Moreover, a chain-extended polymer of poloxamer 407 (Pluronic® F 127) and hexamethylene diisocyanate (HMDI) has been described (cf. Jiang J., Malal R., Li C., Lin M. Y., Colby R. H., Gersappe D., Rafailovich M. H., Sokolov J. C., Cohn D.: Rheology of Thermoreversible Hydrogels from Multiblock Associating Copolymers. Macromolecules 2008; 41:3646-3652).

Since poloxamers are biologically inert, they were soon used as suppositories for pharmaceuticals and, with the emergence of regenerative medicine, also as cell carriers (cf. Kamil S. H., Eavey R. D., Vacanti M. P., Vacanti C. A., Hartnick C.: Tissue-engineered cartilage as a graft source for laryngotracheal reconstruction—A pig model. Arch. Otolaryngol. 2004; 130(9):1048-1051).

The particular advantage of these hydrogels resides in the described thermo-sensitive behaviour. A minimally-invasive application of incorporated cells is thus conceivable. The latter can be easily introduced in the liquid state. After implantation, gel formation occurs due to the change in temperature, which causes the cells to be maintained at the desired location (cf. Cohn D., Lando G., Sosnik A., Garty S., Levi A.: PEO-PPO-PEO-based poly(ether ester urethane)s as degradable reverse thereto-responsive multi-block copolymers. Biomaterials 2006; 27(9):1718-1727; Nguyen M. K., Lee D. S. Injectable biodegradable hydrogels. Macromol. Biosci. 2010; 10(6):563-579).

The use of thermoreversible hydrogels is advantageous, for example, in the treatment of burns. The hydrogel allows the transdermal or local delivery of an active substance and maintains a high degree of moisture on the surface of the skin. This prevents dehydration. In addition, the hydrogel adheres to a considerable degree to the damaged tissue and has a certain elasticity, thereby avoiding a separation of the hydrogel and absorbing, at the same time secretions emerging from the wound. Generally, hydrogels promote healing, as they pass quickly to the gel state at the wound site and maintain moisture in the wound.

While most poloxamers with low polymer concentrations only form gels with poor mechanical properties, chain-extended poloxamers achieve greater stability of the gels. Initial attempts to extend the chains were performed with acrylic acid esters (acrylates). This causes linking moieties with C=C double bonds to the poloxamer. Thereafter, chemical addition reactions were carried out so that a plurality of poloxamer moieties could be connected. Derivatives of acrylic acid are physiologically not harmless. If the chain extension is performed by diisocyanates, the individual poloxamers are linked by urethane moieties. Polyurethanes have been used for a long time as medical implants owing to their tissue compatibility. A further disadvantage to date has been the lack of biological recognition of the material by the cells, which were up to now unable to adhere to the material.

It is thus the object of the present invention to provide chain-extended hydrogels based on poloxamers which do not have the known disadvantages of the prior art, and which are suitable for medical applications. It is further the object of the invention to provide thermoreversible hydrogels which are capable of releasing a biologically-active agent or active substance. In addition, it is the object of the invention to provide thermoreversible hydrogels containing biological material and living cells, wherein the cells adhere to the biological material, and therapeutic applications therefor.

SUMMARY OF THE INVENTION

The above object is attained by providing the chain-extended poloxamer according to claims 1 to 8, the thermoreversible hydrogel according to claims 9 to 21, the application system according to claims 22 to 24, the medical use of the thermoreversible hydrogel according to claims 25 to 34, and the in-vitro process according to claims 35 and 36.

BRIEF DESCRIPTION OF THE DRAWINGS

In FIG. 1a the relative turbidity is in this context plotted against the polymer concentration in wt.-%, in FIG. 1b the mean shelf life module is plotted against the temperature, in FIG. 1c the mean penetration resistance is plotted against the temperature, in FIG. 1d the strength of the gels is plotted against the temperature, and in FIG. 1e the mean proportion released for a protein as biological material is plotted against time.

FIGS. 2a and 2b show images which illustrate cell survival at different polymer concentrations (2.4%, 5% and 10%) of the thermoreversible hydrogel consisting of poloxamer 403, chain-extended by using butane diisocyanate, hereinafter also referred to as "BDI-hydrogel. Different polymer concentrations were in this context initially examined hourly (in FIG. 1a, columns "0h" to "5h"), then daily (in FIG. 2b, columns "1d", "2d" and "3d") and finally, after one week (in FIG. 2b, column "7d") by means of the "Live/Dead-Assay".

DETAILED DESCRIPTION OF INVENTION

Figure 1A:
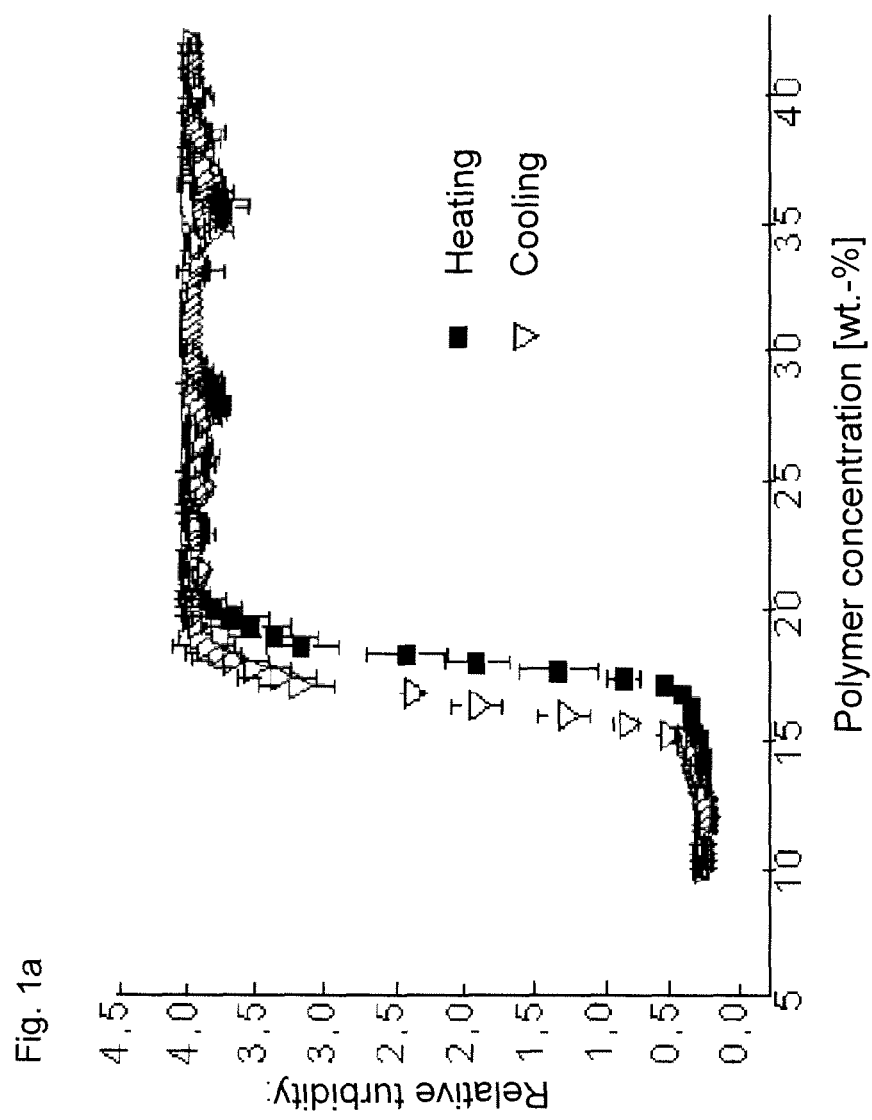
FIGS. 1a to 1e show the physical properties of thermoreversible hydrogels which were prepared from poloxamers which were chain-extended by using diisocyanates, wherein poloxamer 403 or Pluronic P 123 (PMT001), chain-extended by using hexamethylene diisocyanate, poloxamer 403 (PMT002; BDI-hydrogel) chain-extended by using butane diisocyanate, and poloxamer 403 (PMT003), chain-extended by using methylene biscyclohexyl diisocyanate, were examined. These measurements were performed as part of a cooperation project in the laboratory of Prof. Dr. W. Friess at the Centre for Drug Research of the Ludwig Maximilian University of Munich.

The present invention provides chain-extended poloxamers which are prepared from poloxamers using diisocyanates. These chain-extended poloxamers can be converted to thermoreversible hydrogels, which may be used in various ways in the medical field.

Poloxamers useful in the invention, which can be converted to hydrogels at a later stage, are generally those in which the molecular weight of the poloxamer P exceeds 4000 Da. Preferably, the molecular weight of the polypropylene block exceeds 2350 Da. In a preferred embodiment, the proportion of the polyethylene oxide moieties in the above-mentioned poloxamer or, respectively, the above-mentioned poloxamers is 20% to 80%, more preferably 20% to 70% and particularly preferably 20% to 60%. A chain-extended poloxamer P*, prepared by reacting at least one poloxamer P with a diisocyanate, consisting of two polyoxyethylene blocks PEG and one polyoxypropylene block PPG, wherein the molecular weight of the polypropylene oxide block of P is greater than 2350 Da is particularly suitable for the present invention. If there are more than one poloxamers, e.g. two different poloxamers P and P', each poloxamer meets the above requirements.

In particular, for obtaining the chain-extended poloxamer according to the invention, in the above-cited cases having a molecular weight of the poloxamer P of at least 11,000 Da and a proportion of polyethylene oxide in P exceeding 60%, an additional poloxamer, different from the aforesaid poloxamer, is used. Poloxamer 407 (Pluronic® F 127), may serve as an example of poloxamers having a molecular weight of 11,000 Da and a content of polyethylene oxide exceeding 60%. In the present invention, therefore, in the case of using poloxamer 407, preferably at least one poloxamer, different from poloxamer 407, is used in combination.

In another embodiment, for a molecular weight of the above poloxamer P of at least 11,000 Da and a content of polyethylene oxide in P exceeding 60%, the diisocyanate is selected from the group consisting of diisocyanates represented by the formula $O=C=N-(CH_2)_n-N=C=O$ where n=4, 5 or n>6, isophorone diisocyanate, methylene di (4,4'-isocyanato)cyclohexane ($H_{12}$-MDI), lysine diisocyanate and aromatic diisocyanates, preferably diphenyl methane diisocyanate (MDI). In a preferred embodiment, if poloxamer 407 is used, the latter is chain-extended, combined, if necessary, with additional poloxamers and with a diisocyanate, selected from the aforegoing.

Preferably, at least three repeat units of at least one poloxamer P are reacted.

The poloxamer moieties are reacted with a diisocyanate for chain extension. While aromatic diisocyanates can be used for the present invention, which are generally preferred for the present field due to their high reactivity, there is a disadvantage that they may be degraded to carcinogenic diamines. By contrast, corresponding degradation in aliphatic diisocyanates would result, for example, in diamines, such as putrescine or cadaverine, which occur to a small extent in the metabolic processes of the body. In addition, the aliphatic compounds are also resistant to other degradation reactions, which is why they are used in technical applications, if yellowing or the like is to be avoided. Therefore, aliphatic and, in particular, linear diisocyanates are preferred according to the invention.

The commercially-available poloxamers (Pluronic® or Lutrol®) differ in the ratio of ethylene oxide or polyethylene glycol-(PEG) moieties a and polypropylene oxide or (PPG-) moieties b, and in the length of the blocks. This results in different behaviour in water.

If a poloxamer, as described above, is reacted with a diisocyanate, the chain-extended poloxamer P* of the present invention, particularly if it comes to a single poloxamer as starting material, contains the following structural unit:

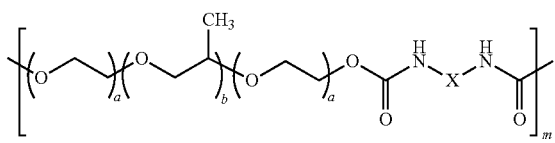

wherein a and b are each whole numbers between 1 and 110, and m≥3; a denotes the number of repeat units of the polyethylene oxide) block PEG, and b denotes the number of repeat units of the polypropylene oxide) block PPG; prepared from a diisocyanate of the formula O=C=N—X—N=C=O, wherein X is the aliphatic or aromatic moiety of the diisocyanate. If two different poloxamers (P and P') are concerned as the starting material, the chain-extended poloxamer P* likewise has structural units represented by the formula

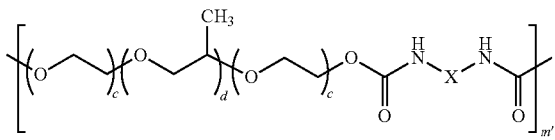

and/or the formula

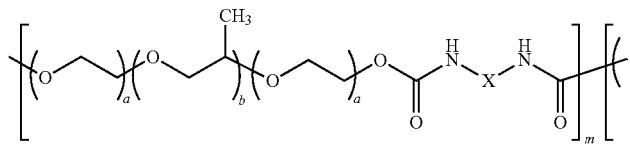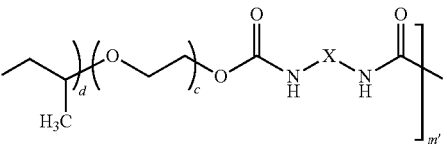

wherein a, b, m and X are as defined above, c represents the number of repeat units of the poly(ethylene oxide) block PEG and d denotes the number of repeat units of the poly(propylene oxide) block PPG, respectively referred to in the second poloxamer P', wherein c and d are each whole numbers between 1 and 110, and m'≥3.

In a preferred embodiment, the chain-extended poloxamer(s) P is/are selected from one or a plurality of poloxamers 272, 278, 331, 333, 334, 335, 338, 401, 402, 403 and 407 (trade names: Pluronic® or Lutrol® L 92, F 98, L101, P 103, P 104, P 105, F 108, L 121, L 122, P 123 and F 127). The poloxamer 407 is preferably used in combination with one or a plurality of other poloxamer(s), In a further preferred embodiment, the poloxamer 407 is reacted in combination with further poloxamers, or even alone with linear diisocyanates of the formula O=C=N—(CH$_2$)$_n$—N=C=O where n=4, 5 or n>6, or with aliphatic diisocyanates, such as isophorone diisocyanate, methylene di(4,4'-isocyanato)cyclohexane (H$_{12}$-MDI) or lysine diisocyanate, or aromatic diisocyanates, preferably diphenylmethane diisocyanate (MDI).

The poloxamers of the present invention may generally be in liquid, paste-like or solid form. For example, under ordinary conditions, the poloxamers 272, 331, 401 and 402 (or the Pluronic-types marked with "L") are liquid, the poloxamers 333, 334, 335 and 403 (or the Pluronic-types marked with "P") are paste-like, and the poloxamers 278, 668 and 407 (or the Pluronic-types marked with "F") are solid.

Thermoreversible hydrogels based on poloxamer 403, 407 and 338 are particularly preferred according to the invention.

To date, mainly poloxamer 407 or "Pluronic® F 127" (according to the above general formula where a=100, b=65; i.e. [PEG]$_{65}$[PPG]$_{100}$[PEG]$_{65}$) was used in hydrogels for medical and pharmaceutical purposes.

According to the invention, it is also possible to combine a plurality of poloxamers P to form a chain-extended poloxamer P*. Chain-extended poloxamers P* consisting of two or three different poloxamers are preferred in this case.

According to the invention the chain-extended poloxamers P* may be reacted to thermoreversible hydrogels. The thermoreversible hydrogel of the present invention is preferably a thermoreversible hydrogel which
  (a) includes the above chain-extended poloxamer P* and
  (b) a biological material, selected from the group consisting of an antibiotic, antimicrobial or antifungal active substance, proteins, glucosaminoglycans, lysozyme and a polyamino acid.

The thermoreversible hydrogel of the present invention is obtainable by
  (a) forming the above-mentioned chain-extended poloxamer P*, and
  (b) mixing the chain-extended poloxamer with a biological material, selected from the group consisting of an antibiotic, antimicrobial or antifungal active substance, proteins, glucosaminoglycans, lysozyme and a poly amino acid.

Aromatic and aliphatic, in particular linear diisocyanates, which have proved particularly advantageous as chain extenders, are preferred as diisocyanates.

As mentioned above, the lack of biological recognisability of the material by the cells is disadvantageous according to the state of the art, since the said cells have to date been unable to adhere to the material. More particularly, the invention is based on the exemplary idea to react the hydrogel based on a chain-extended poloxamer with collagen as a biological material, and on the discovery of the surprisingly advantageous properties of the thermoreversible hydrogel prepared therefrom. According to a preferred embodiment, finely ground or soluble collagen, for example, may be used as biological material. Laboratory experiments have shown that the cells within a certain tolerance range exhibit an expanded cell morphology, suggesting an adherence to collagen.

According to the invention it was found that, for example, even from the relatively hydrophobic poloxamer 403 (Pluronic® F 123) in low concentrations, versatile thermoreversible hydrogels with appropriate physical properties can be produced, especially when, as described above, these are chain-extended with linear or aliphatic diisocyanates. These hydrogels have proved particularly valuable as an application system for cells and high molecular weight proteins. The hydrogels according to the present invention exhibit greatly-improved properties compared with hydrogels which are based on well-known chain-extended poloxamers. Thus, a particular advantage of the thermoreversible hydrogels based on poloxamer 403, compared with those based exclusively on poloxamer 407 (Pluronic® F 127) is that they are more stable in vivo.

In order to obtain longer cell survival and biological functionality of the integrated cells, the hydrogels are modified with biological material according to the invention. In doing so, the cells obtain adhesion points to which they can adhere by way of integrin binding. Such adhesion is a prerequisite for the cell activity (cf. Popov C., Radie T., Haasters F., Prall W. C., Aszodi A., Gullberg D. et al.: Integrins alpha2beta1 and alpha11 beta1 regulate the survival of mesenchymal stem cells on collagen I. Cell Death Dis. 2011; 2: e186).

According to the invention, suitable biological materials are selected from the group consisting of an antibiotic, antimicrobial or antifungal active substance, proteins, glucosaminoglycans, lysozyme and a polyamino acid. The antibiotic, antimicrobial or antifungal active substance is preferably selected from β-lactam-antibiotics, tetracyclines, aminoglycosides, macrolides, antivirals, allylamines, antimycotic antibiotics, imidazoles and derivatives thereof. The polyamino acid is preferably selected from natural and synthetic polyamino acids.

In a preferred embodiment, the biological material is selected from the class of proteins.

According to the invention, the protein is preferably selected from the group consisting of a protein inhibiting or stimulating cell growth and cell differentiation; or from the group consisting of fibrin, gelatine, collagens, and bone-morphogenetic proteins (BMP). The protein may further be a growth factor, and is preferably selected from the group consisting of the insulin-like growth factor (IGF), the transforming growth factor (TGF), the platelet-derived growth factor (PDGF), the epidermal growth factor (EGF), the fibroblast growth factor (FGF), the granulocyte-macrophage colony-stimulating factor (GMCSF), the vascular endothelial growth factor (VEGF), the hepatocyte growth factor (HGF), interleukin-1B (IL-1B), interleukin-8 (IL-8), the nerve growth factor (NGF) and haematopoietic growth factors such as erythropoietin and colony-stimulating factors such as G-CSF.

In a preferred embodiment, the biological material is selected from β-lactam antibiotics, tetracyclines, aminoglycosides, macrolides, antivirals, allylamines, antimycotic antibiotics, imidazoles and derivatives thereof, the epidermal growth factor (EGF), the TGF-β-(transforming growth factor beta)-superfamily, preferably the BMP (bone morphogenetic protein)- and GDF (growth differentiation factor)-families, more preferably BMP2, BMP7 and GDF-5.

In a preferred embodiment, the biological material consists of soluble collagen, finely-ground collagen, gelatine, human blood, animal blood, components of human or animal blood.

In a preferred embodiment, the biological material consists of collagen type I, II or III.

In a preferred embodiment, the biological material or protein is a hormone or enzyme, more preferably follistatin or myostatin.

The protein can also be an immunoglobulin or an antibody, preferably selected from the group consisting of IgA, IgD, IgE, IgM, IgG, IgY and IgW.

Moreover, if the biological material is a glucosaminoglycan, hyaluronan (hyaluronic acid) may be used.

The thermoreversible hydrogel of the present invention may also comprise living cells.

The aforementioned cells are preferably selected from the group consisting of mononuclear cells, in particular mesenchymal stem cells, progenitor cells and cells differentiated therefrom, such as osteoblasts, adipocytes, chondrocytes, fibroblasts, epithelial cells, myoblasts, tendocytes, or mononuclear haematopoietic stem and progenitor cells and cells differentiated therefrom, such as immune cells, or multinucleated cells such as giant cells, macrophages and osteoclasts.

In a further preferred embodiment, the cells are genetically modified or modified in the gel.

In a preferred embodiment, the thermoreversible hydrogel may also contain a tracer. In this context, tracers made of radioactive substances are preferred which can be visualised by PET or SPECT. Examples of such tracers are radioisotopes such as tritium, $^{14}c$, $^{18}F$, $^{32}P$, $^{35}S$, $^{111}In$ and $^{123}I$.

Surprisingly, it has now been found that in thermoreversible hydrogels of the invention, due to the connection with biological material, an expanded cell morphology of incorporated cells occurs, which gives rise to the formation of integrin binding to the biological material (e.g. collagen), and at the same time the mechanically-advantageous properties of the thermoreversible hydrogel are hardly modified.

The thermoreversible hydrogel of the present invention allows a wide range of applications in the medical field. Accordingly, the present invention provides a thermoreversible hydrogel for medical use, the said medical use being drug delivery or a biomedical application.

In a preferred embodiment, the invention provides an application system, which includes the above-mentioned thermoreversible hydrogel. In this embodiment, the aforesaid application system preferably further comprises a therapeutic agent which stimulates or inhibits cell/tissue growth or kills cells.

A large number of therapeutic agents may be introduced by using the thermoreversible hydrogels of the present invention. Examples include the above-mentioned agents for the biological material, as well as generally synthetic inorganic and organic compounds, proteins and peptides, polysaccharides and other sugars, lipids, gangliosides and nucleic acid sequences having therapeutic, prophylactic or diagnostic activities. Nucleic acid sequences include genes, antisense-molecules which bind to complementary DNA by inhibiting transcription, and ribozymes. The therapeutic agents to be incorporated can have a variety of biological activities, such as vasoactive agents, neuroactive agents, hormones, anticoagulants, immunomodulators, cytotoxic agents, antibiotics, antiviral agents, antisense agents, antigens and antibodies. Proteins which include antibodies or antigens, anticalins or similar artificial proteins which are capable of binding antigens, may likewise be introduced. Proteins are defined as consisting of 100 amino acid residues or more; peptides are fewer than 100 amino acid residues, Unless otherwise stated, the term 'protein' denotes both protein and peptides. Examples include insulin, parathormone, parathormone fragments, irisin, myostatin, follistatin and other hormones.

Specific therapeutic agents include antibiotics, antiviral agents, both steroidal and non-steroidal anti-inflammatory agents, antineoplastics, antispasmodics, including channel blockers, modulators of cell/extracellular matrix interactions which include cell growth inhibitors and anti-adhesion molecules, enzymes and enzyme inhibitors, anticoagulants and/or antithrombin agents, growth factors, DNA, RNA, inhibitors of DNA, RNA or protein synthesis, compounds modulating the proliferation and/or the growth of cells, vasodilation agents and other medicinal substances, which are commonly used for the treatment of tissue lesions. Specific examples of these compounds include angiotensin-converting enzyme inhibitors, prostacyclin, heparin, salicylates, nitrates, calcium channel blockers, streptokinase, urokinase, tissue plasminogen activator (TPA) and anisoylated plasminogen activator (TPA) and anisoylated plasminogen-streptokinase-activator complex (APSAC), colchicine and alkylating agents and aptamers. Specific examples for modulators of cell interactions include interleukins, platelet-derived growth factor, acidic and basic fibroblast growth factor (FGF), transforming growth factor β, (TFG β), epidermal growth factor (EGF), insulin-like growth factor and antibodies for these. Specific examples of nucleic acids include genes and cDNAs coding for proteins, expression vectors, antisense and other oligonucleotides, such as ribozymes which can be used to regulate or prevent gene expression. Specific examples of other biologically-active agents include modified components of the extracellular matrix or receptors thereof and lipid and cholesterol sequestration agents.

Examples of proteins as therapeutic agents also include cytokines, such as interferons and interleukins, proteins and colony-stimulating factors. Carbohydrates as therapeutic agents include Sialyl Lewis$^x$, for which it has been shown that it binds to receptors for selectins while inhibiting inflammation. A "deliverable growth factor equivalent" (abbreviated DGFE), a growth factor for a cell or tissue can be used, which is broadly constructed such that it includes growth factors, cytokines, interferons, interleukins, proteins, colony-stimulating factors, gibberellins, auxins and vitamins; furthermore including peptide fragments or other active fragments of the above; and further including vectors, i.e. nucleic acid constructs with the ability to synthesise such factors in the target cells, whether by transformation or transient expression; and further including effectors which stimulate or suppress the synthesis of such factors in the tissue, in which case these include natural signal molecules, antisense and triple helical nucleic acids and the like. Examples of DGFEs are vascular endothelial growth factor (VEGF), endothelial cell growth factor (ECGF), basic fibroblast growth factor (bFGF), bone growth protein (BMP) and platelet-derived growth factor (PDGF) and DNAs encoding the same. Examples of clot-dissolving agents are tissue plasminogen activator, streptokinase, urokinase and heparin.

Drugs with antioxidant activity (i.e. which destroy active oxygen or prevent the formation thereof) may also be provided as therapeutic agents in the thermoreversible hydrogel of the present invention, useful, for example, in the prevention of adhesions. Examples include superoxide dismutase, or other protein drugs include catalases, peroxidases and general oxidases or oxidative enzymes such as cytochrome P450, glutathione peroxidase and other native or denatured haemoproteins.

Mammalian stress response proteins or heat shock proteins such as heat shock protein 70 (hsp 70) and hsp 90 or the stimuli which inhibit or reduce the expression of stress response proteins or heat shock proteins, such as flavonoids, may also be provided in the hydrogel as therapeutic agents.

In a further preferred embodiment, the aforesaid application system based on the thermoreversible hydrogel of the present invention further includes an oxygen-releasing substance. The oxygen-releasing substance is, in this context, preferably present in combination with enzymes. Examples of the enzyme include superoxide dismutase, catalases, peroxidases and general oxidases or oxidative enzymes such as cytochrome P450, glutathione peroxidases and other native or denatured haemoproteins.

An application system of the present invention with oxygen-releasing substances is described in Example 8 below.

The object of the addition of oxygen-releasing substances to the gel is to prevent cell death from lack of oxygen in larger constructs until new blood vessels have formed which can supply the cells. The supply by means of diffusion works, at the most, across a few millimeters. If exclusively peroxides and cells are added to the thermoreversible hydrogel according to the invention, the cells the by the action of the hydrogen peroxide produced. However, if a peroxide-degrading enzyme such as catalase is added, cell death can be prevented.

The present invention further provides the above-mentioned thermoreversible hydrogel for use in the manufacture of a medicament for the treatment of a medical condition, the said medicament serving for applying an aqueous solution of the thermoreversible hydrogel onto tissue in vivo.

In a preferred embodiment, the aforesaid aqueous solution comprises a solution or suspension of a biologically-active material.

In a preferred embodiment, the aforesaid medical condition is a burn or abrasion of the skin.

In another preferred embodiment, the aforesaid medical condition is a tissue, disturbed by a surgical procedure. In a preferred embodiment, the aforesaid surgical intervention is a vertebroplasty or kyphoplasty.

The application of the thermoreversible hydrogel of the present invention may also be effected by using known techniques, such as laparoscopy and endoscopy. Known catheter systems, such as described, for example, in U.S. Pat. Nos. 5,328,471 or 5,213,580, may also be employed.

In a preferred embodiment the aforesaid medical use is characterised in that the surgical procedure is performed through the cannula of a trocar.

In a preferred embodiment, for the aforesaid medical use, the thermoreversible hydrogel is applied to tissue in a pharmaceutically-acceptable carrier. Saline or phosphate-buffered saline are examples of such carriers.

In a preferred embodiment, for the aforesaid medical use, the thermoreversible hydrogel is provided in a pharmaceutically-acceptable carrier for parenteral administration.

In a preferred embodiment, for the aforesaid medical use, the thermoreversible hydrogel is located on a surface of a biological tissue, or on a surface of a medical device. In addition, the thermoreversible hydrogel may be located between opposing surfaces, thereby creating a tendency for the surfaces to adhere to one another.

In a preferred embodiment, for the aforesaid medical use, the biological tissue is an organ. In the aforementioned embodiment, for the aforesaid medical use, the organ is selected preferably from skin, a visceral organ, tissue of the musculoskeletal system, preferably bone, cartilage, connective tissue, preferably tendons and fatty tissue.

Finally, the present invention provides an in-vitro method for forming a composition on a surface, which comprises the application of an aqueous solution of the above-mentioned thermoreversible hydrogel, mixtures thereof, or the above-mentioned medical application system onto the surface.

Preferably, the in-vitro method comprises the application of an aqueous solution of the above-mentioned, thermoreversible hydrogel containing living cells.

More preferably, the in-vitro method is performed, using the aforesaid application systems, notably an application system comprising living cells and an oxygen-releasing substance and an enzyme. In this context, calcium peroxide is preferably used as the oxygen-releasing substance. Catalase, for example, is preferred as the enzyme.

In a particularly preferred embodiment of the above in-vitro method, the thermoreversible hydrogel of the invention is prepared from poloxamer 403 (Pluronic® P 123).

The following examples illustrate the preparation and properties of the chain-extended poloxamers or thermoreversible hydrogels obtained therefrom according to the present invention.

EXAMPLES

Example 1: Preparation of Poloxamer, Chain-Extended by Using Hexamethylene Diisocyanate In a glass flask with reflux condenser 17.4 g of poloxamer 403 (Pluronic® P 123; 3 mmol) are made up to 80 g with dry toluene. This is stirred with a magnetic stirring bar at about 45° C. until a clear solution is obtained. 20 ml of toluene are distilled off in order to remove traces of water. Subsequently, by means of a syringe, 0.49 g of hexamethylene diisocyanate (HDI, 2.92 mmol) and a solution of 120 µl of 1,8-diazabicyclo[5.4.0]undec-7-ene (DBU) in 2 ml of toluene are added in each case. The temperature is raised to 55° C. After 2 hrs, the toluene is removed using a rotary evaporator. Subsequently, drying takes place at 45° C. (water bath) under fine vacuum conditions until weight constancy is obtained.

Example 2: Preparation of Poloxamer, Chain-Extended by Using Butane Diisocyanate In a glass flask with reflux condenser 17.4 g of poloxamer 403 (3 mmol) are made up to 80 g with dry toluene. This is stirred with a magnetic stirring bar at about 45° C. until a clear solution is obtained. 20 ml of toluene are distilled off in order to remove traces of water. Subsequently, by means of a syringe, 0.373 g of butane diisocyanate (BDI, 2.92 mmol) and a solution of 120 µl of 1,8-diazabicyclo[5.4.0]undec-7-ene (DBU) in 2 ml of toluene are added in each case. The temperature is raised to 55° C. After 2 hrs, the toluene is removed using a rotary evaporator. Subsequently, drying takes place at 45° C. (water bath) under fine vacuum conditions until weight constancy is obtained.

Example 3: Preparation of Poloxamer, Chain-Extended by Using Methylene Diphenyl Diisocyanate 17.4 g poloxamer 403 (3 mmol) are weighed into a glass flask with reflux condenser. 63 g of dried toluene are added. Agitation at 45° C. until a clear solution is obtained. 30 ml of toluene are distilled off, in order to remove traces of water. Subsequently, by means of a syringe, 0.738 g of diphenyl-methane diisocyanate (MDI, 2.92 mmol) and a solution of 120 µl of 1,8-diazabicyclo[5.4.0]undec-7-ene (DBU) in 2 ml of toluene are added in each case. The temperature is raised again to 45° C. After 2 hrs, the toluene is removed using a rotary evaporator. Subsequently, drying takes place at 45° C. (water bath) under fine vacuum conditions until weight constancy is obtained.

Example 4: Preparation of Poloxamer, Chain-Extended by Using Hexamethylene Diisocyanate from Three Different Poloxamers 11.6 g poloxamer 403 (Pluronic P 123; 2 mmol), 12.5 g poloxamer 407 (Pluronic® F-127; 1 mmol) and 14.6 g poloxamer 338 (Pluronic® F-108, 1 mm) are weighed into a glass flask with reflux condenser and made up to 90 g with dried toluene. This is stirred with a magnetic stirring bar at about 45° C. until a clear solution is obtained. 20 ml of toluene are distilled off in order to remove traces of water. Subsequently, by means of a syringe, 0.665 g of hexamethylene diisocyanate (HMDI, 3.95 mmol) and a solution of 120 µl of 1,8-diazabicyclo[5.4.0]undec-7-ene (DBU) in 5 ml of toluene are added in each case. The temperature is raised to 55° C. After 2 hrs, the toluene is removed using a rotary evaporator. Subsequently, drying takes place at 45° C. (water bath) under fine vacuum conditions until weight constancy is obtained. A relatively solid polymer is obtained, which dissolves well in water at temperatures below 10° C.

Even a 10% solution of the resultant polymer solidifies on heating to 35° C. and yields a transparent gel.

The chain-extended poloxamer obtained in Example 4 from three different poloxamers has the advantage, with respect to a chain-extended poloxamer which is prepared exclusively from poloxamer 403 (Pluronic® P 123) that it is transparent and solidifies at low concentrations. Compared to a chain-extended poloxamer which is prepared exclusively from poloxamer 407 (Pluronic® F 127), it should be emphasised that the new material does not dissolve in the supernatant culture medium, even after several days at 37° C.

Example 5: Properties of Thermoreversible Hydrogels Made from Chain-Extended Poloxamers The materials show two characteristic changes in the temperature range between 15° and 35° C. When starting heating from 4° C. onwards, at first turbidity of the previously transparent liquids (sol) occurs between 15° and 20° C. In FIG. 1a the behaviour of a thermoreversible hydrogel of 10% of a poloxamer 403 chain-extended by using hexamethylene diisocyanate is represented here.

Figure 1B:
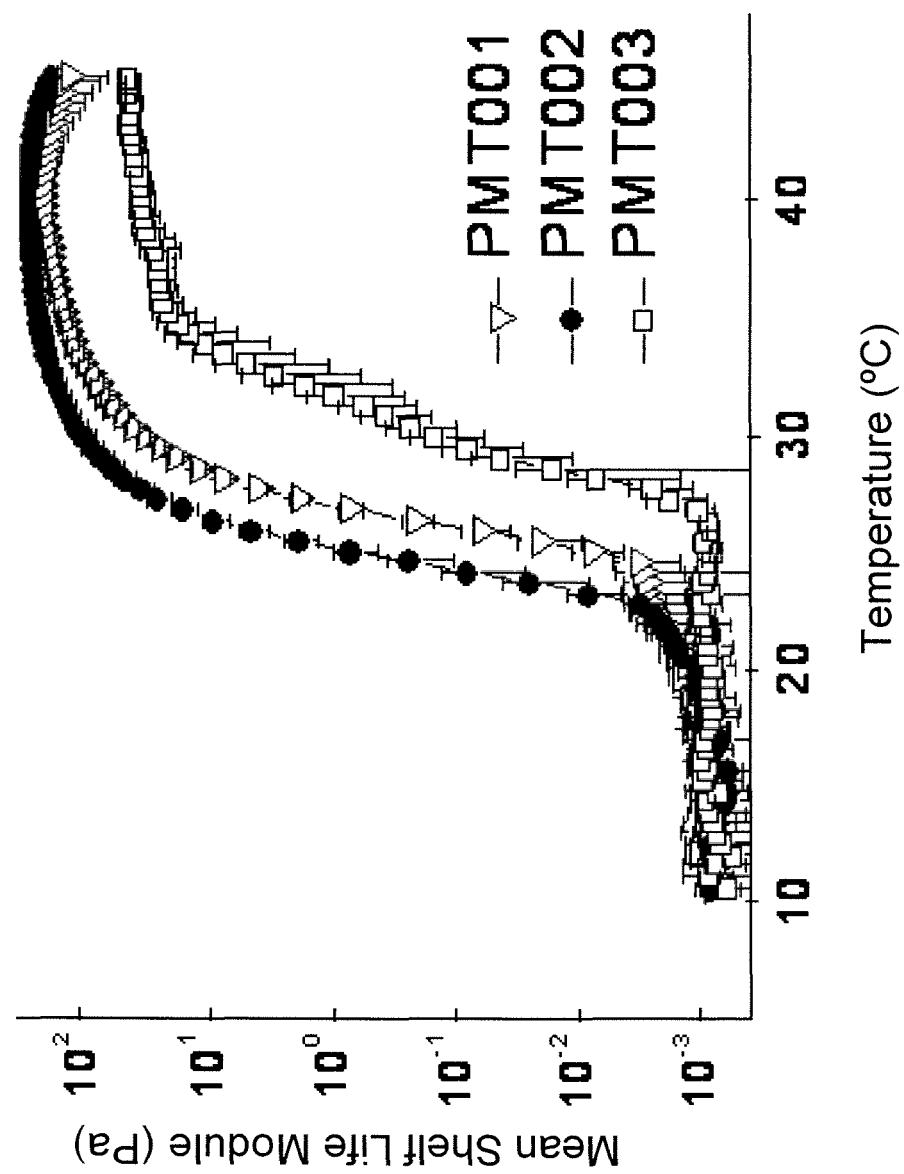

Between 22° and 35° C. the viscosity then rises by several orders of magnitude. By way of example FIG. 1b shows respectively 10% solutions of poloxamer 403 (referred to as PMT0001), chain-extended by using hexamethylene diisocyanate, poloxamer 403 (PMT002), chain-extended by using butane diisocyanate and poloxamer 403 (PMT003), chain-extended by using methylene biscyclohexyl diisocyanate. The latter has fewer repeat units.

Figure 1C:
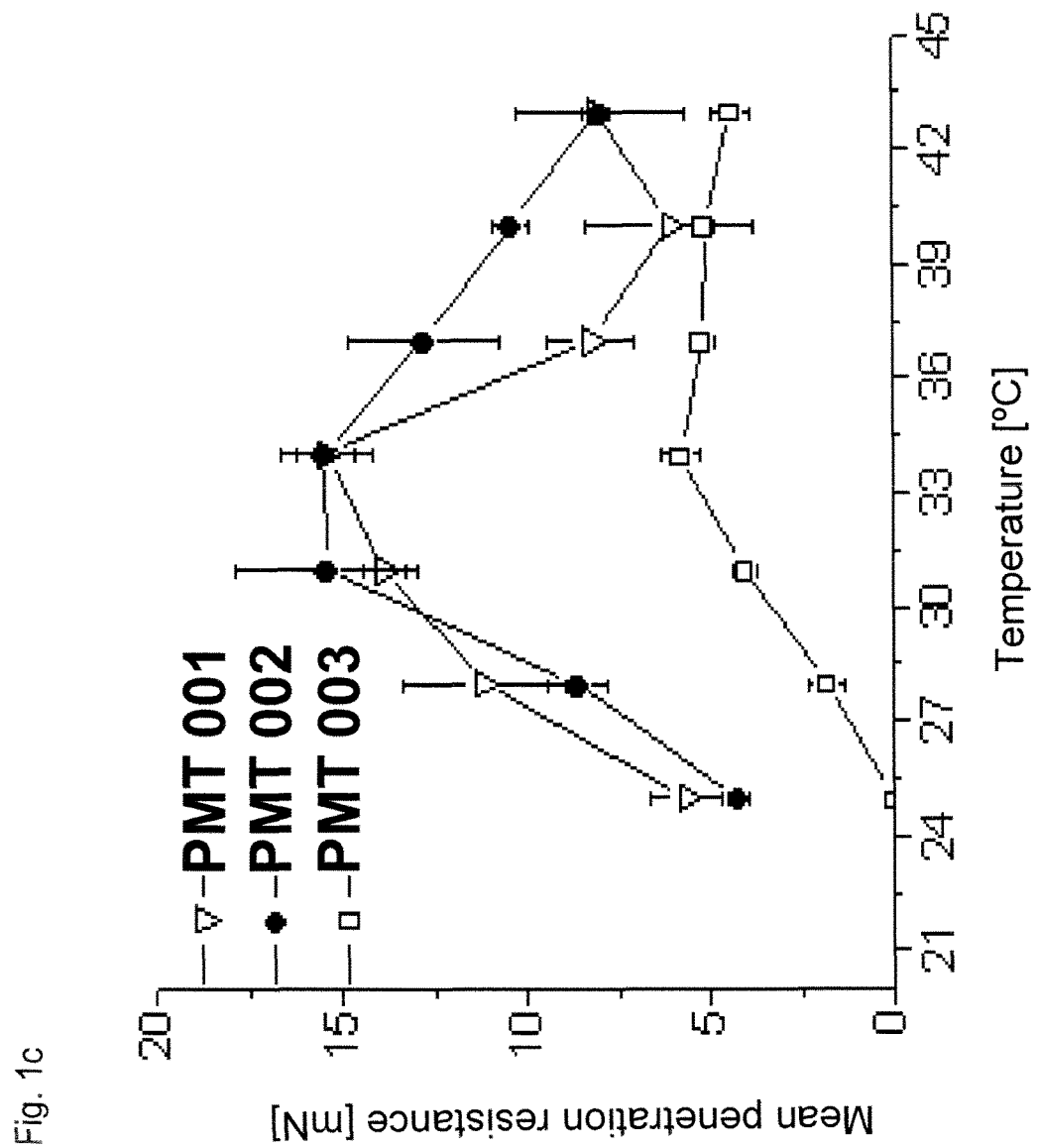

FIG. 1c shows for the same thermoreversible hydrogels PMT001 to PMT003 that the penetration resistance has a similar pattern with a clear peak between 30° and 35° C.

Figure 1D:
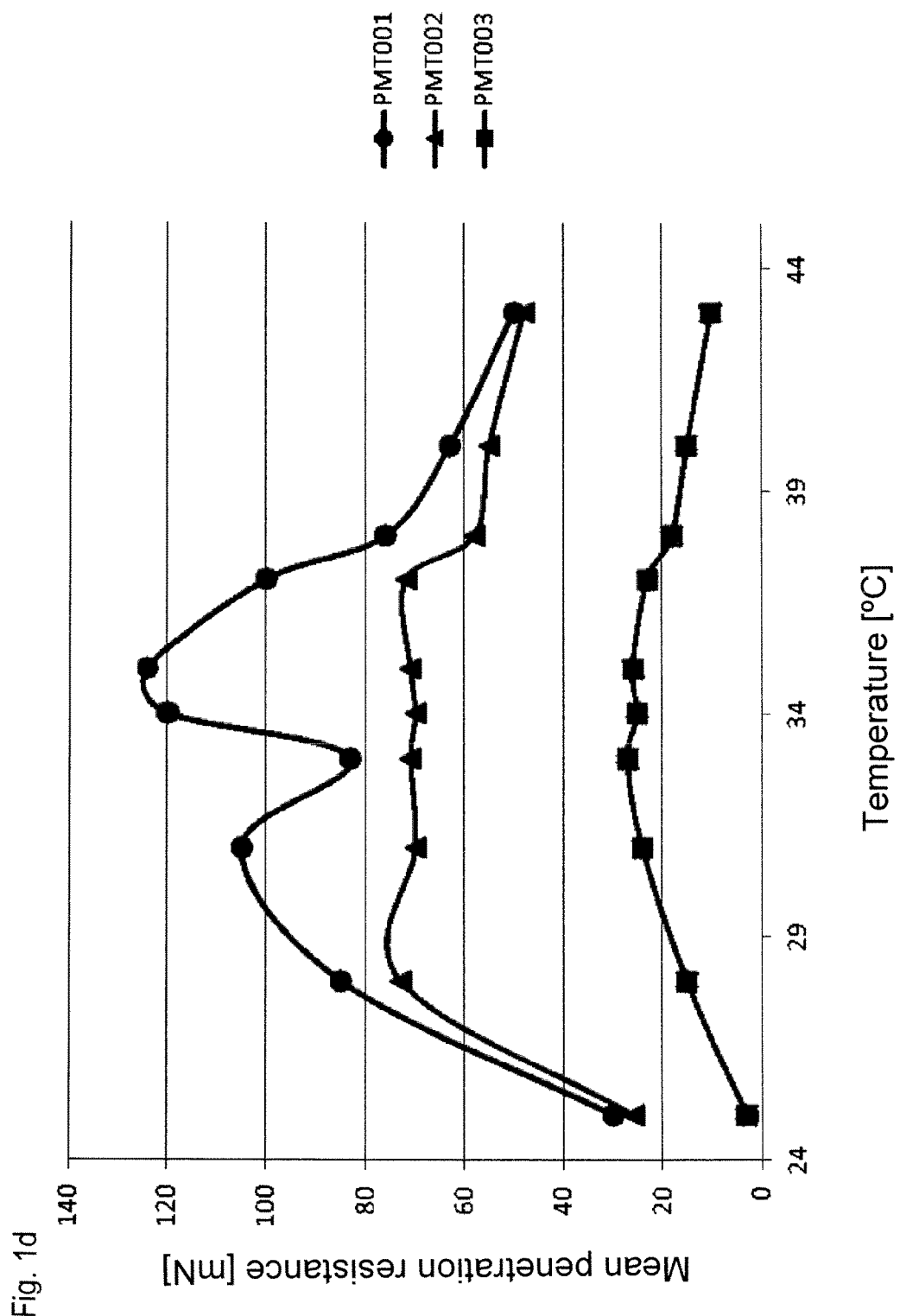

FIG. 1d shows that with increasing concentration, as expected, the strength of the gels (25%) increases.

Figure 1E:
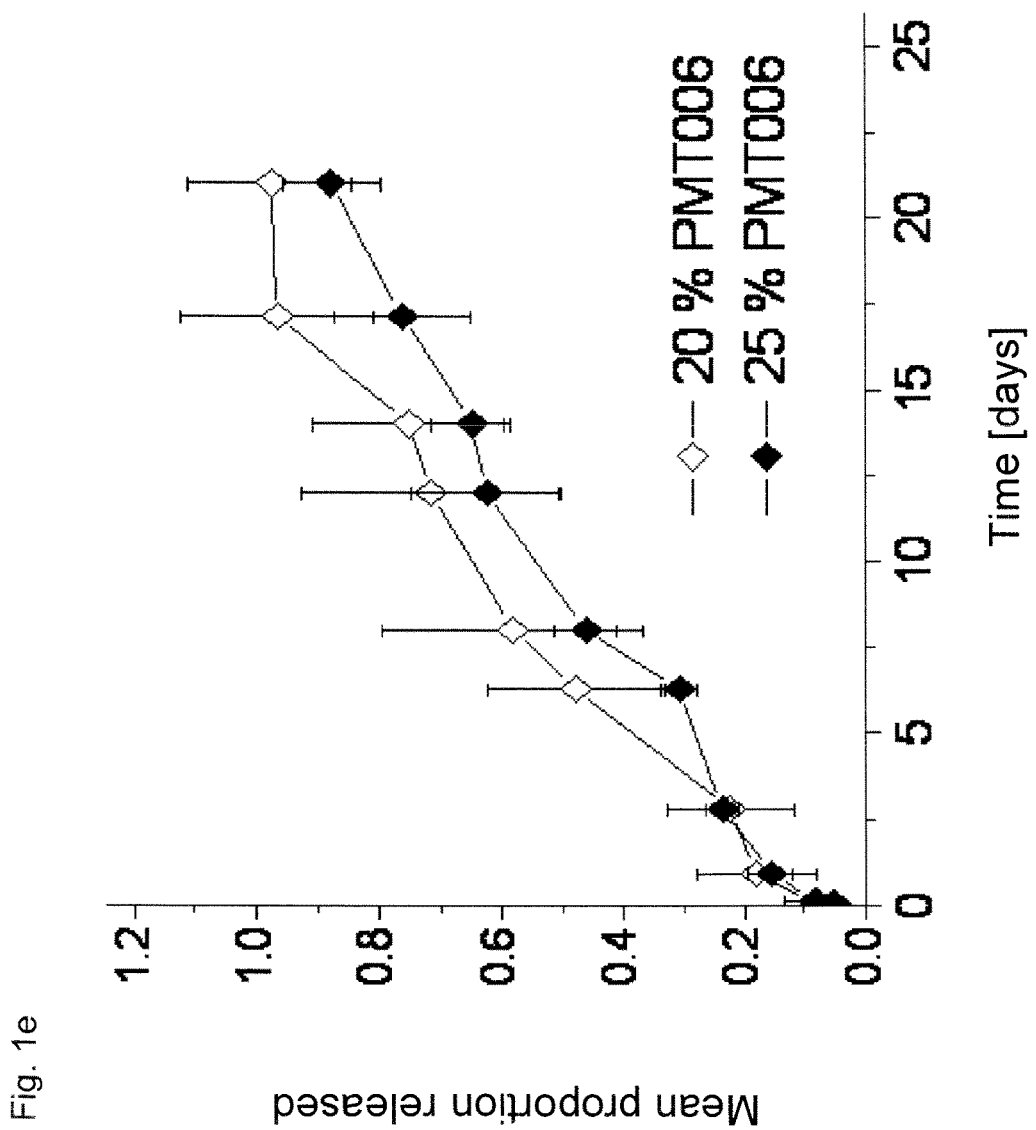

FIG. 1e shows that the gels are suitable for uniform protein release over several weeks. In the measurement shown, poloxamer 403, chain-extended by using hexamethylene diisocyanate was used at concentrations of 20% and 25%, respectively.

Example 6: Effect of Gel Concentration

The desired amount of the chain-extended poloxamer (polymer) is weighed in under sterile conditions and mixed with the appropriate amount of cell culture medium. Both are stored in a syringe at 4° C. for several days and stirred again and again. This causes the formation of a homogenous solution which gels at 25 to 30° C. At about 15° C., 100,000 immortalised stem cells per milliliter are added. The cell number is determined in a Neubauer counting chamber, the cells are centrifuged into a pellet in a Falcon tube and then added to the mixture. Different polymer concentrations (2.5%, 5% and 10%) are examined first hourly, then daily and finally after one week by means of the "Live/Dead-assay". Microscopic studies are performed both at the bottom and in the interior of the sample. Cell survival for a 10% polymer concentration is, in this context, somewhat lower than for the lower concentrations. The strength of the gel, on the other hand, is considerably higher.

Figure 2A:
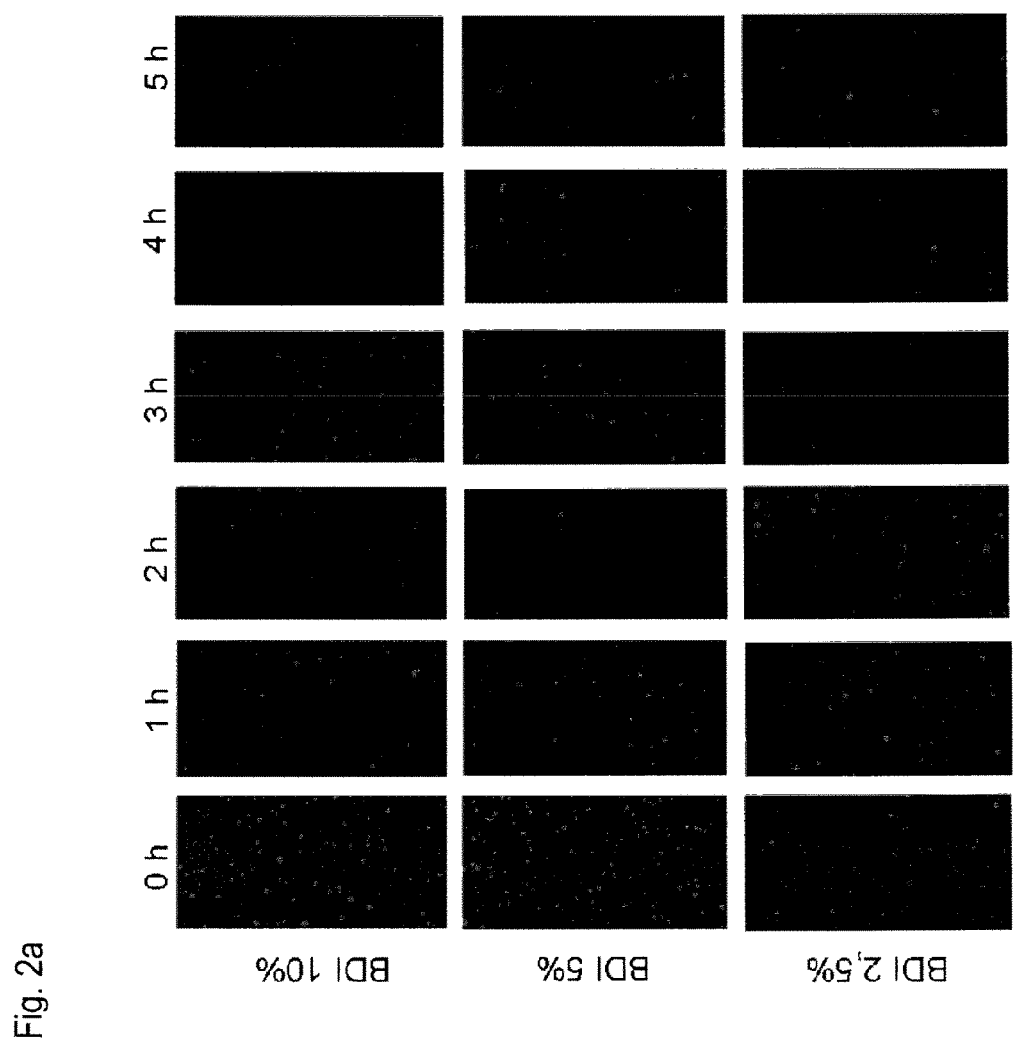
Figure 3:
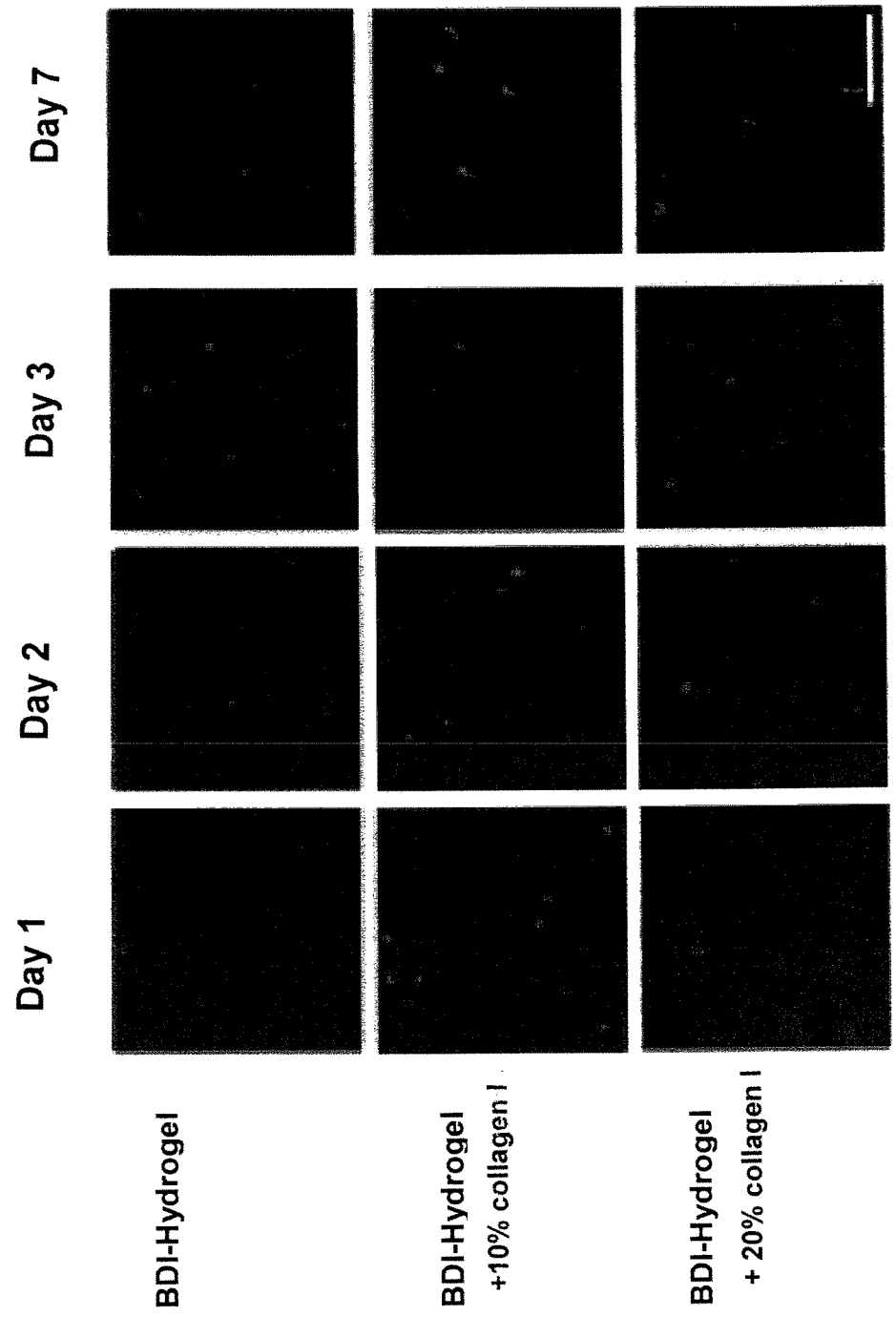
FIG. 3 shows the cell morphology in a thermoreversible BDI-hydrogel of the invention with 10%, 20% or without collagen, in each case after 1, 2, 3 and 7 days. The scale is 200 μm; all images were taken at the same level of magnification.

The results are shown in FIGS. 2 and 3.

Example 7: Effect of the Biological Material Using the Example of Collagen

In order to demonstrate the high biological activity of the thermoreversible gel with biological material, a series of experiments was performed, in which 100,000 immortalised stem cells per milliliter were cultured at various concentrations (0%, 10% and 20%) of soluble collagen in a 10% hydrogel according to the invention. The culture is carried out at 37° C. in a humid atmosphere with 5% carbon dioxide and 95% air. The vitality was determined over 7 days by means of the "Live/Dead-assay. In addition, the cell morphology was examined by using a confocal laser scanning microscope. The results are shown in FIG. 4 and FIG. 5

1. A 10% solution of the polymer of poloxamer 403, chain-extended by 1,4-butane diisocyanate (cf. Example 2) in a cell culture medium is prepared as described above. 100,000 eGFP-SCP1 cells are suspended in 1 ml of this solution. The cell number was determined in a Neubauer counting chamber, the cells are centrifuged into a pellet in a Falcon tube and then transferred into the gel. After 1, 2, 3 and 7 days the samples are studied. The cell survival (cf. FIG. 4, left-hand side) is acceptable at 45% after 7 days, but the cells show a round morphology which does not indicate an increased adherence of the cells, as the latter can only be concluded from expanded cell morphology.
2. The procedure is as above, however 10% soluble collagen from rat tails ("Coll type I-rat tail", Merck) are added to the solution (cf. FIG. 4, centre). In this case, cell survival is considerable at about 40% after 7 days. After only 3 days the typical elongated morphology of the cells becomes apparent.
3. The procedure is as in 2., only this time 20% collagen are introduced into the mixture (cf. FIG. 4, right-hand side). Cell survival is excellent at 80%. The cells exhibit an even more pronounced elongated morphology.

Figure 4:
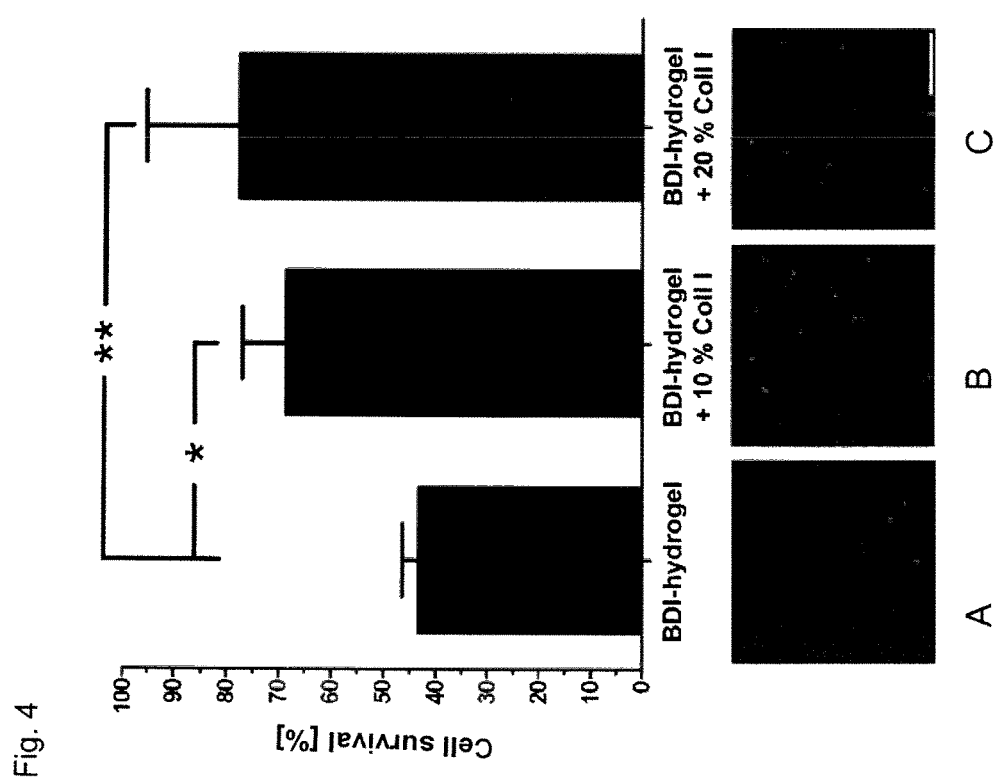
FIG. 4 shows micrographs which illustrated the cell survival of eGFP-SCP1s after 7 days in the thermoreversible BDI-hydrogel of the present invention with or without collagen I (MW±SD, r=3, n=3). The Kruskal-Wallis-statistics using the multiple comparison test by Dunn provided significant differences between the thermoreversible hydrogel of the invention without (A) or with collagen I (B and C). In this context, $\alpha=0.05$, $*p<0.05$, and $**p<0.01$. Exemplary micrographs (at the bottom, 10× magnification) after staining with propidium iodide (PI); the scale is 200 μm.

FIG. 4 shows the respective micrographs, illustrating cell survival of eGFP-SCP1s after 7 days in the thermoreversible hydrogel of the present invention with or without collagen I. Significant differences between thermoreversible hydrogel of the invention without or with collagen I become visible. Exemplary micrographs at the bottom (10× magnification) after staining with propidium iodide; the scale (graduation mark) is 200 μm.

Figure 5:
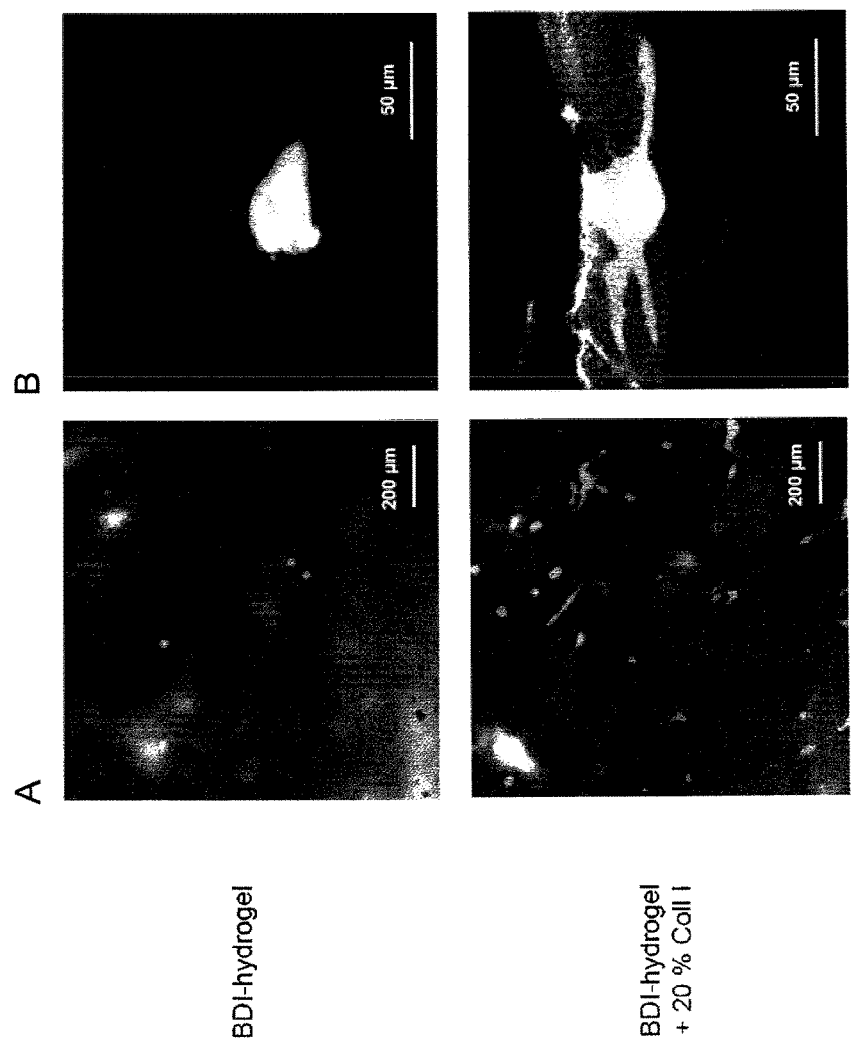
FIG. 5 shows eGFP-SCP1s cells after 7 days in the thermoreversible BDI-hydrogel of the present invention (referred to in the figure as "BDI-hydrogel) with or without 20% collagen I, visualised by confocal laser scanning microscopy. The images were taken at a level of 10× magnification (scale: 200 μm; images A) or 63× (scale: 50 μm; images B).

FIG. 5 shows eGFP-SCP1s cells after 7 days in the thermoreversible hydrogel (referred to as "BDI-hydrogel" in the figure) with or without 20% collagen I, visualised by confocal laser scanning microscopy. The images were taken with a magnification of 10× (left side) or 63× (right side).

Figure 6A:
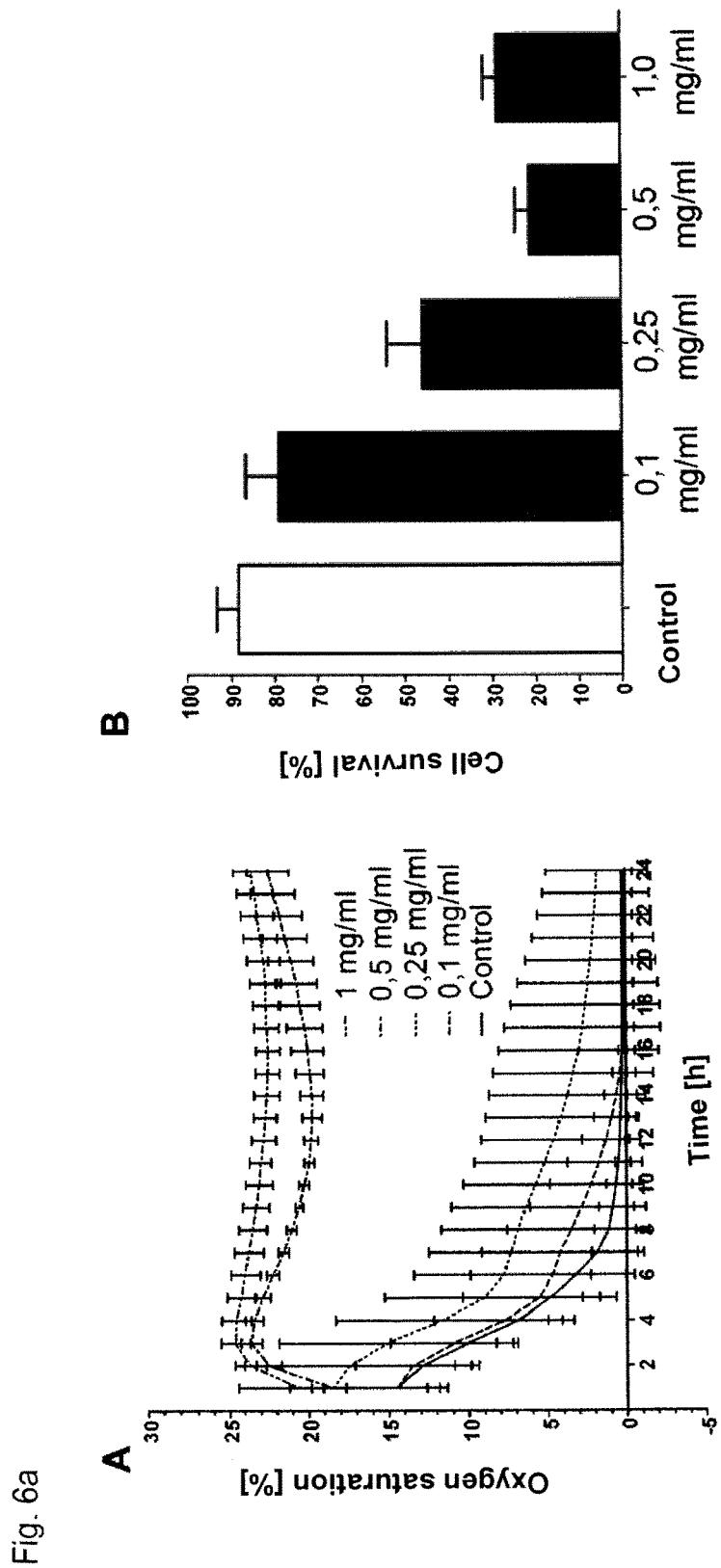
FIG. 6a shows the oxygen saturation (A) or cell survival (B) after 24 h culturing in syringes in BDI-hydrogel with $CaO_2$, "control" represents BDI-hydrogel without $CaO_2$ (MW±SD, r=3, n=1).

Example 8: Effect of Oxygen on Cell Survival in the Application System a) Application system having different concentrations of an oxygen-releasing substance ($CaO_2$) without an enzyme.

hTERT-immortalised human mesenchymal stem cells were cultured in syringes containing thermoreversible hydrogel, which was obtained from poloxamer 403 and butane diisocyanate (i.e. "BDI-hydrogel") at concentrations of 1 mg/ml, 0.5 mg/ml, 0.25 mg/ml and 0.1 mg/ml of calcium peroxide ($CaO_2$), and the oxygen saturation was determined at hourly intervals. The cell survival rates were subsequently determined by vitality assays. The results are shown in FIG. 6a.

b) Application system containing an oxygen-containing substance ($CaO_2$) and different concentrations of the enzyme.

Figure 6B:
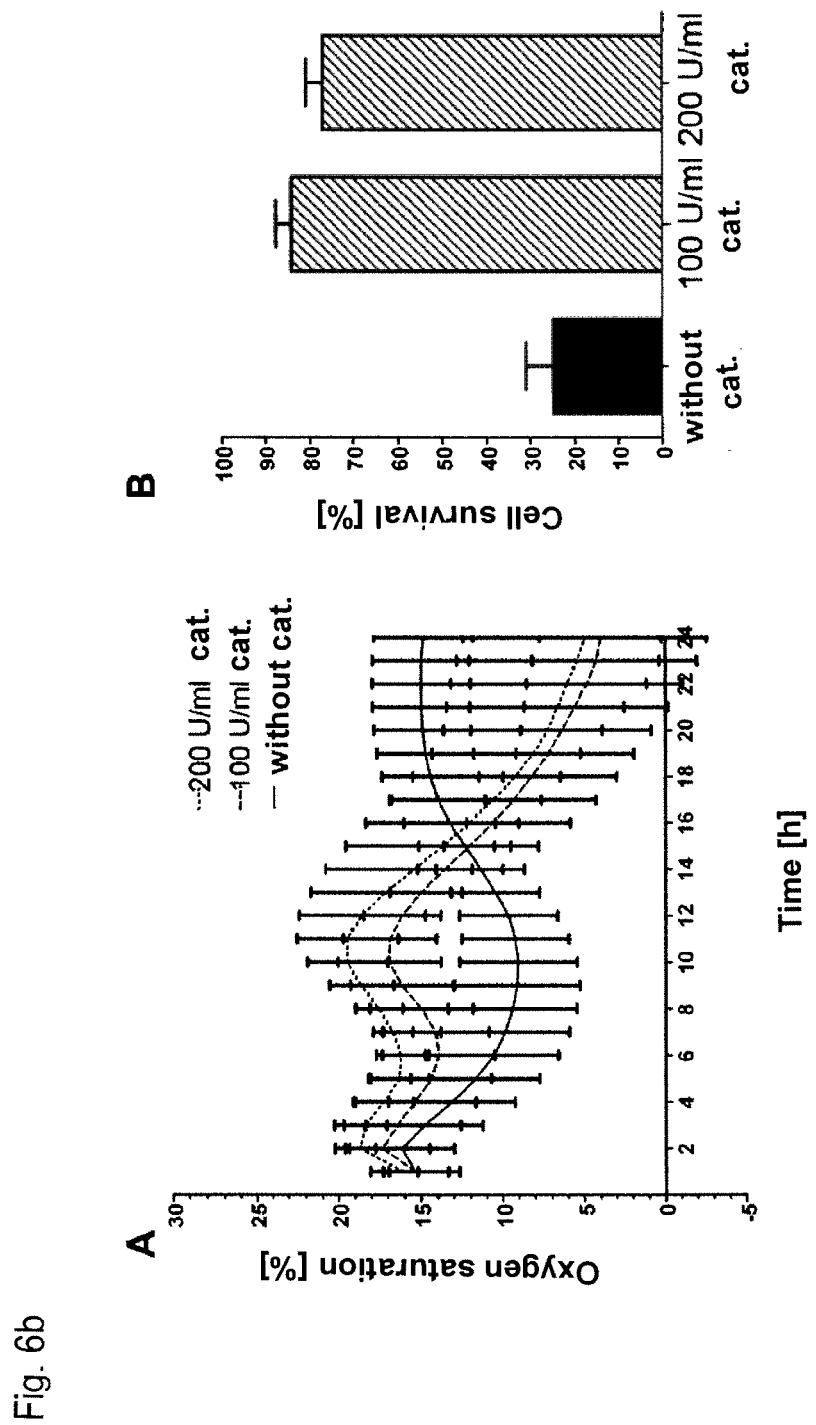
FIG. 6b shows the oxygen saturation (A) and cell survival (B) after 24 h culturing in syringes in BDI-hydrogel with 0.25 mg/ml $CaO_2$ and various catalase concentrations (MW±SD, r=3, n=1).

Example 8a) was repeated, except that 100 U/ml or 200 U/ml or no catalase (control) was added as the enzyme. The results are shown in FIG. 6b, from which it can be seen that catalase concentrations of 100 U/ml or 200 U/ml have a beneficial effect on cell survival.

c) Application system having different concentrations of an oxygen-releasing substance at a constant enzyme concentration.

Figure 6C:
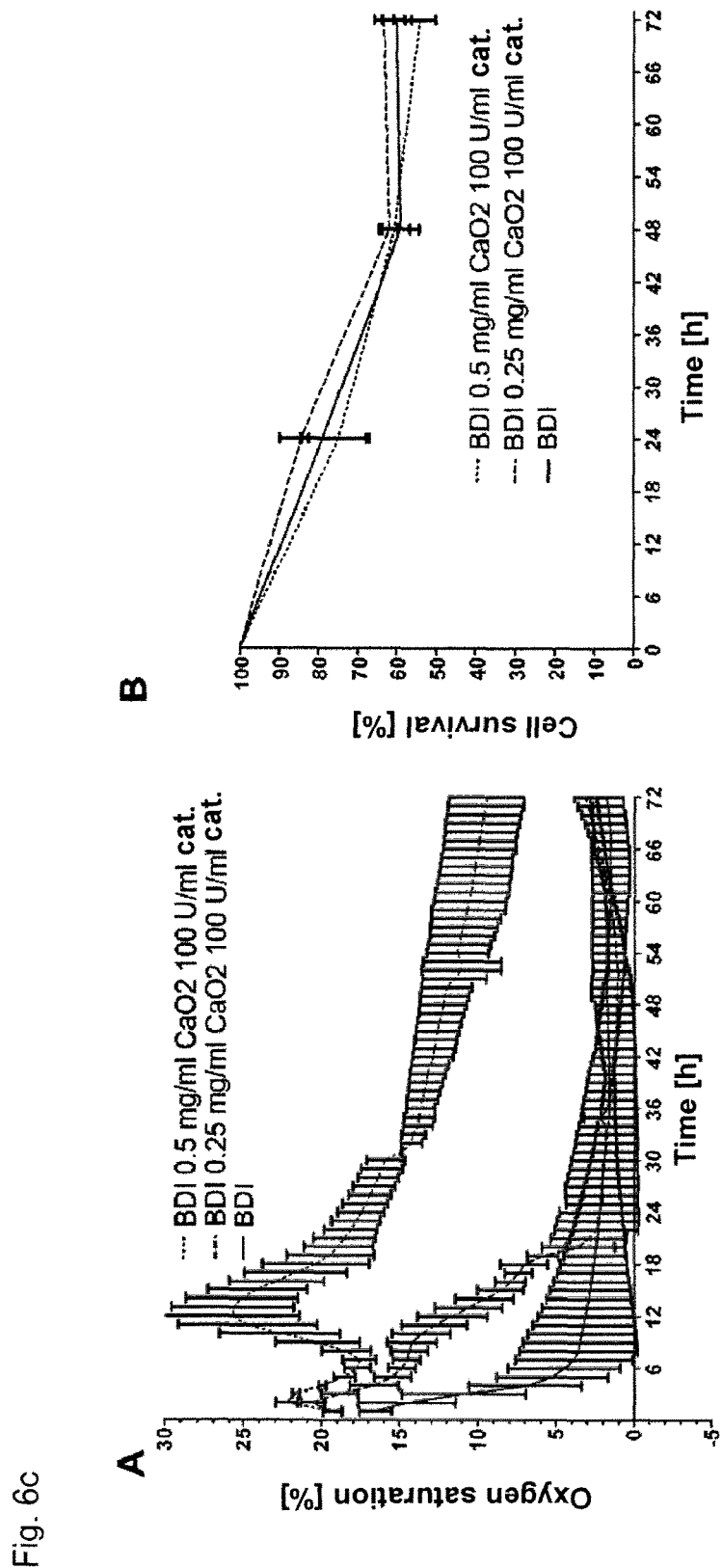
FIG. 6c shows the oxygen saturation (A) and cell survival (B) after 72 h culturing in syringes in BDI-hydrogel with 0.5 mg/ml $CaO_2$ and 100 U/ml catalase or BDI-hydrogel in concentrations of 0.25 mg/ml $CaO_2$ and 100 U/ml catalase, (MW±SD, r=3, n=1).

Analogously to Example 8b), the oxygen saturation (A) and cell survival (B) was measured after 72 h of being cultured in syringes in BDI-hydrogel with 0.5 mg/ml $CaO_2$ and 100 U/ml catalase or BDI-hydrogel with 0.25 mg/ml $CaO_2$ and 100 U/ml catalase. The results are shown in FIG. 6c, from which can be seen that at a concentration of 0.25 mg/ml $CaO_2$ and a catalase concentration of 100 U/ml cell survival, even after 72 hours, with a value of about 70% is improved compared with the control denoted as "BDI-hydrogel".

The invention claimed is:

1. A thermoreversible hydrogel composition comprising:
   a) a chain-extended poloxamer represented by Formula I:

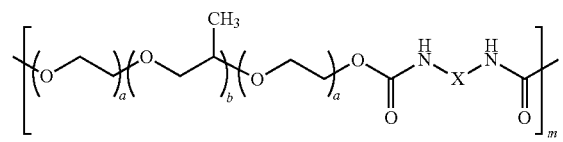

Formula I wherein m≥3, a denotes the number of repeat units of the poly(ethylene oxide) block and is 20, b denotes the number of repeat units of the poly(propylene oxide) block and is 70, and X represents an aliphatic or aromatic moiety;
   b) a therapeutically effective amount of collagen; and
   c) a pharmaceutically acceptable carrier,
   wherein the ratio of collagen to chain-extended poloxamers in the thermoreversible hydrogel composition is from 1:1 to 2:1.

2. The thermoreversible hydrogel composition of claim 1 wherein the pharmaceutically acceptable carrier comprises saline.

* * * * *